US00PP18670P2

(12) United States Plant Patent
Bradford

(10) Patent No.: US PP18,670 P2
(45) Date of Patent: Mar. 25, 2008

(54) INTERSPECIFIC TREE NAMED 'PLUMSWEET VIII'

(50) Latin Name: *Prunus*
Varietal Denomination: PLUMSWEET VIII

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/634,857

(22) Filed: Dec. 7, 2006

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP14,196 P2 9/2003 Bradford
PP14,219 P2 10/2003 Bradford

*Primary Examiner*—Kent Bell
*Assistant Examiner*—S. B. McCormick-Ewoldt

(57) ABSTRACT

The present invention relates to an interspecific tree and more particularly to a new and distinct variety broadly characterized by a medium size, vigorous, hardy, and fairly productive tree. Being self-unfruitful, the present variety requires cross pollination from an apricot, interspecific, or plum that blooms during the mid season. The fruit matures under the ecological conditions described during early to mid August, with first picking on Aug. 10, 2006. The fruit is uniformly medium to large in size, a green and red two-tone in skin color, clingstone in type, globose to oblate in shape, red in flesh color, very firm in texture, and outstanding in flavor.

1 Drawing Sheet

Botanical classification: *Prunus* sp.
Varietal denomination: 'PLUMSWEET VIII'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'PLUMSWEET VIII'.

During a typical blooming season I isolate as seed parents both individual and groups of different plum trees by covering them with a screen house. A hive of bees is placed inside each such house, and bouquets to provide pollen from different plum, apricot, and interspecific plum-apricot hybrid trees are placed in buckets near the trees approximately every two days for the duration of the bloom. During 2001 one such house containing an unnamed red plum was crossed by me in this manner. To pollinate this red plum, I selected bouquets from several sources of apricot and interspecific plum-apricot hybrid trees without keeping specific written details. Upon reaching maturity the fruit from this red plum tree was harvested, and the seeds were removed, cracked, stratified and germinated as a group with the label "H175". They were grown as seedlings on their own root in my greenhouse and upon reaching dormancy transplanted to a cultivated area of my experimental orchard located near Le Grand, Calif. in Merced County (San Joaquin Valley). During the summer of 2004 the claimed variety was selected by me as a single plant from the group of seedlings described above. Subsequent to origination of the present variety of intespecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to 'PLUMSWEETTWO' (U.S. Plant Pat. No. 14,196) plum by being self-unfruitful and by producing fruit that is globose to somewhat oblate in shape, red in flesh color, and clingstone in type, but is distinguished therefrom by producing fruit that is larger in size, a two-tone red and green in skin color, and that matures about six days later.

SUMMARY OF VARIETY

The present interspecific variety is characterized by a medium size, vigorous, hardy, and fairly productive tree. Being self-unfruitful, the present variety requires cross pollination from an apricot, interspecific, or plum that blooms during the mid season, such as 'Plumsweetone' (U.S. Plant Pat. No. 14,219) plum. The present variety's abundance of blossoms and pollen entices strong bee activity to facilitate pollination. The fruit matures under the ecological conditions described during early August, with first picking on Aug. 10, 2006, and will hang on the tree for about fifteen more days. The fruit is uniformly medium to large in size, a green and red two-tone in skin color, clingstone in type, globose to oblate in shape, red in flesh color, very firm in texture, and outstanding in flavor.

DRAWING

The accompanying photograph consists of four whole fruits positioned to display the characteristics of the skin color and form, one fruit divided transversely to the suture plane to reveal the flesh and stone, and typical leaves.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley); Calif. The fruit description was developed at the state of firm ripe on Aug. 16, 2006, on the original tree during its fifth growing season. The flower and bud description were developed during the previous blooming season. All major color code designations are by reference to the Inter-Society Color Council, National Bureau of Standards. Common color names are also used occasionally.

Parentage:
- *Seed parent.*—Unnamed red plum.
- *Pollen parent.*—Unknown.

Tree

Size: Medium, reaching and maintaining a height of 9' [2.74 m.] and a spread of 7' [2.13 m.] after five growing seasons utilizing typical dormant pruning.

Vigor: Medium, responding typically to irrigation and fertilization. The variety grows about 4' [1.22 m.] of surplus top-growth during the spring and summer. The plant should be grown on a standard commercial rootstock for production purposes.

Growth: Spreading and dense.

Form: Pruned to a vase form.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Medium productive, thinning usually required.

Fertility: Self-unfruitful, requiring cross pollination by a suitable mid seasonal blooming apricot, interspecific, or plum, such as 'Plumsweetone' (U.S. Plant Pat. No. 14,219).

Bearing: Uncertain bearer, dependent upon favorable weather during the blooming period.

Trunk:
- *Size.*—Medium, reaching a maximum diameter of 4" [102 mm.] after the fifth growing season.
- *Texture.*—Rough.
- *Bark color.*—A Brownish gray [64. brGy] and Deep brown [56. deep Br] variegation with Light yellowish brown [76. l.yBr] crevices present.
- *Lenticels.*—Approximate Number Per Square Inch: 15. Color: Deep orange yellow [69. deep OY]. Typical Size: 1/8" [3.2 mm.] to 7/16" [11.1 mm.]. Shape: Eye-shaped to elongated.

Branches:
- *Size.*—Diameter of limb is 2¼ [57 mm.] measured 12" above the crotch, 1⅛" [29 mm.] measured 12" above the first fork.
- *Texture.*—Smooth on first and second year wood, increasing roughness with age.
- *Color.*—1st Year Wood Topside: Light reddish brown [42. l.rBr]. 1st Year Wood Underside: Brilliant yellow green [116. brill.YG]. Older Wood: Deep yellowish brown [75. deep yBr].
- *Lenticels.*—Number Per Square Inch: More than 40 on second year wood. Color: Light yellowish brown [76. l.yBr]. Typical size: 1/64" [0.4 mm.] to 3/32" [2.4 mm.]. Shape: Elongated.

Leaves:
- *Size.*—Medium. Average Length: 3½" [89 mm.]. Average width: 1⅝" [41 mm.].
- *Arrangement.*—Alternate.
- *Thickness.*—Medium.
- *Form.*—Elliptical.
- *Apex.*—Acuminate.
- *Base.*—Obtuse with an average angle of 100 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: ⅝" [15.9 mm.]. Average Thickness: 1/16" [1.6 mm.]. Color: Light yellow green [119. l.YG] with some Grayish red [19. gy.R] streaking with exposure to the sun.
- *Stipules.*—Number: Usually 2 per leaf, up to 6 per growing tip. Average Length: ¼"[6.4 mm.]. Color: Light yellow green [119. l.YG] becoming Grayish reddish brown [46. gy.rBr] with age.
- *Glands.*—Number: Usually 2 per leaf. Position: Mostly alternate, positioned at the intersection of the petiole and the base of the blade. Size: Small. Form: Globose. Color: Light yellow green [119. l.YG] becoming Deep reddish brown [41. deep rBr] in the center with age.
- *Leaf buds.*—Pointed, medium.

Flower buds:
- *Hardiness.*—Hardy, with respect to central California winters.
- *Diameter.*—Typically 3/16"[4.8 mm.] 1 week before bloom.
- *Length.*—Typically ⅜"[9.5 mm.] 1 week before bloom.
- *Form.*—Not appressed.
- *Surface.*—Pubescent.
- *Color.*—White [263. White].

Flowers: Perfect, complete, perigynous, usually a single pistil, typically thirty or more stamens, five sepals and petal locations alternately positioned.
- *Average flower diameter.*—1 1/16"[27.0 mm.].
- *Number of petals.*—Five, no double blossoms observed.
- *Petal shape.*—Oval to circular.
- *Petal margin.*—Smooth to slightly wavy.
- *Average petal diameter.*—½" [12.7 mm.].
- *Average petal length.*—9/16" [14.3 mm.].
- *Petal apex.*—Rounded.
- *Petal base.*—Obtuse.
- *Petal color.*—White [263. White].
- *Anther color.*—Light yellow [86. l.Y].
- *Stigma color.*—Pale greenish yellow [104. p.gY].
- *Sepal color.*—Brilliant yellow green [116. brill.YG].
- *Sepal length.*—5/32" [4.0 mm.].
- *Sepal width.*—⅛" [3.2 mm.].
- *Average pistil length.*—½" [12.7 mm.], 25% blank.
- *Average stamen length.*—½" [12.7 mm.].
- *Fragrance.*—Moderate.
- *Pollen production.*—Moderate.
- *Blooming period.*—Medium, three days before 'Plumsweetone' (U.S. Plant Pat. No. 14,219).
- *Onset of bloom.*—One percent on Feb. 20, 2006.
- *Date of full bloom.*—Mar. 6, 2006.

*Duration of bloom.*—One to two weeks, dependent on ambient temperature.
*Bloom density.*—Heavy.
*Number per cluster.*—2 to 9, average 4.

FRUIT

Maturity when described: Firm ripe, Aug. 16, 2006.
Date of first picking: Aug. 10, 2006.
Date of last picking: Aug. 20, 2006.
Size: Uniform, medium to large.
*Average diameter axially.*—2⅜" [60 mm.].
*Average diameter across cheek plane.*—2 9/16" [65 mm.].
*Average diameter across suture plant.*—2 9/16" [65 mm.].
*Typical weight.*—5.1 ounces [145 grams].
Form: Uniform, fairly symmetrical, globose to somewhat oblate.
*Longitudinal section form.*—Elliptical, compressed axially.
*Transverse section through diameter.*—Round.
Suture: An inconspicuous line located in a shallow groove extending from the stem cavity to the pistil point.
Ventral surface: Rounded, very slight lipping.
Lips: Slightly unequal.
Cavity: Flaring, circular, suture showing on one side.
*Depth.*—7/16" [11.1 mm.].
*Breadth.*—1" [25.4 mm.].
Base: Truncate, slightly cordate if viewed parallel to the suture.
Apex: Rounded.
Pistil point: An inconspicuous dot located at the end of the suture.
Stem: Medium.
*Average length.*—⅜" [9.5 mm.].
*Average width.*—⅛" [3.2 mm.].
Skin:
*Thickness.*—Medium.
*Surface.*—Smooth.
*Tenacity.*—Tenacious to flesh.
*Astringency.*—Moderate.
*Tendency to crack.*—None observed.
*Color.*—Dark purplish red [259. d.pR] with Dark greenish yellow [103. d.gY] streaking and freckling stronger toward the apex.
*Bloom.*—Abundant.
Flesh:
*Color.*—Very deep red [14. v.deep R] toward the skin, Dark pink [6. d.Pk] toward the stone.
*Surface of pit cavity.*—Moderate reddish orange [37. m.rO] fibers breaking when twisted from stone.
*Amygdalin.*—Moderate.
*Juice.*—Abundant, rich.
*Texture.*—Firm and crisp.
*Fibers.*—Abundant, fine.
*Ripens.*—Slightly earlier at apex.
*Flavor.*—Acidic and abundantly sweet, 20 to 24 brix.
*Aroma.*—Moderate.
*Eating quality.*—Outstanding.

STONE

Type: Clingstone.
Form: Distorted oval.
Hilum: Narrow, oblong.
Base: Oblique.
Apex: Obtuse with an average angle of 110 degrees and sharp 1/16" [1.6 mm.] tip.
Sides: Equal.
Surface: Rough, with a single groove from the base to apex on each side of the dorsal fin.
External color of stone: Light brown [57. l.Br] when dried.
Pit wall color when cracked: Light yellowish brown [76. l.yBr] toward the exterior with a Pale orange yellow [73. p.OY] line toward the interior.
Cavity surface color: Dark orange yellow [72. d.OY].
Average pit wall thickness: 1/16" [1.6 mm.].
Average width: ⅝" [15.9 mm.].
Average length: ⅞" [22.2 mm.].
Average breadth: 5/16" [7.9 mm.].
Tendency to split: None observed.
Kernel:
*Form.*—Oval.
*Skin color.*—Light yellow [86. l.Y] when freshly removed.
*Pellicle color.*—Grayish yellowish brown [80. gy.gBr].
*Vein color.*—Light grayish yellowish brown [79. l.gy.yBr].
*Taste.*—Not bitter, tolerable to eat.
*Viable.*—Yes.
*Average width.*—7/16" [11.1 mm.].
*Average length.*—9/16" [14.3 mm.].
*Amygdalin.*—Slight.

Use

Market: Fresh market and long distance shipping.
Keeping quality: Good, fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'PLUMSWEETTWO' (U.S. Plant Pat. No. 14,196) plum by being self-unfruitful and by producing fruit that is globose to somewhat oblate in shape, red in flesh color, and clingstone in type, but is distinguished therefrom by producing fruit that is larger in size, a two-tone red and green in skin color, and that matures about six days later.

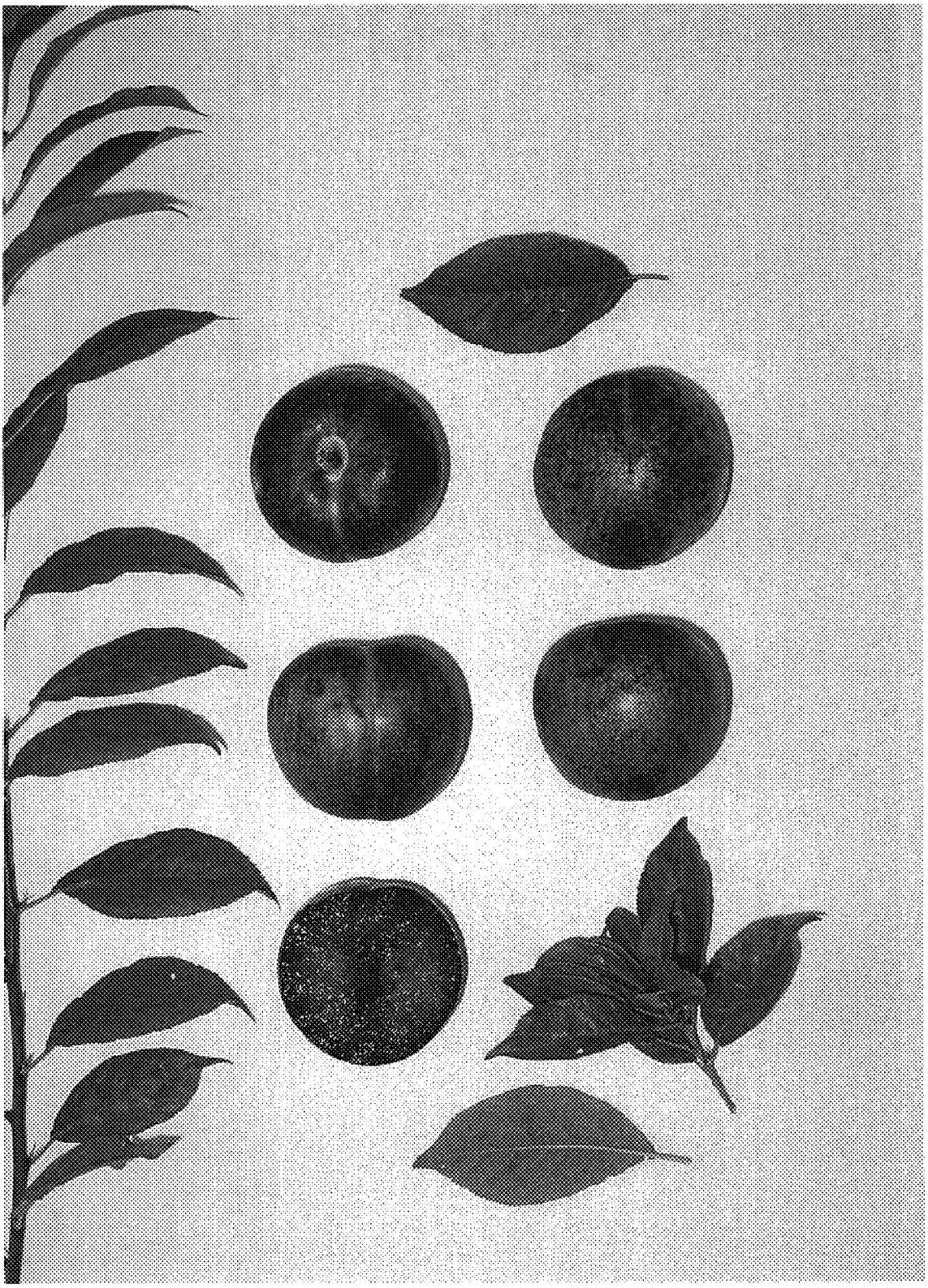

* * * * *